United States Patent [19]

Eidenschink et al.

[11] Patent Number: 4,834,905

[45] Date of Patent: * May 30, 1989

[54] RING COMPOUNDS

[75] Inventors: Rudolf Eidenschink; Joachim Krause, both of Dieburg, Fed. Rep. of Germany; Beatrice M. Andrews, Grimsby, England; George W. Gray, North Humberside, England; Neil Carr, North Humberside, England

[73] Assignees: Merck Patent Gesellschaft mit beschränkter Haftung, Darmstadt, Fed. Rep. of Germany; The Secretary of State for Defence in Her Britannic Majesty's Government of the United Kingdom of Great Britain and Northern Ireland, England

[*] Notice: The portion of the term of this patent subsequent to Dec. 9, 2003 has been disclaimed.

[21] Appl. No.: 915,609

[22] Filed: Oct. 3, 1986

Related U.S. Application Data

[62] Division of Ser. No. 511,609, Jul. 7, 1983, Pat. No. 4,627,933.

[30] Foreign Application Priority Data

Jul. 7, 1982 [DE] Fed. Rep. of Germany ....... 3225290

[51] Int. Cl.[4] .................... G02F 1/13; C09K 19/34; C09K 19/32; C09K 19/30; C09K 19/20; C09K 19/12; C07C 69/62; C07C 69/76
[52] U.S. Cl. .................... 252/299.61; 252/299.62; 252/299.63; 252/299.64; 252/299.65; 252/299.66; 350/350 R; 549/370; 549/372; 549/373; 549/374; 549/375; 558/414; 558/426; 558/427; 558/428; 558/429; 558/430; 558/431; 560/1; 560/55; 560/59; 560/60; 560/65; 560/73; 560/102; 560/105; 560/116; 560/117; 560/118; 560/125; 560/126
[58] Field of Search ........... 252/299.6, 299.63, 299.61, 252/299.62, 299.66, 299.5, 299.65, 299.64, 299.67; 350/350 R; 560/105, 55, 102, 60, 106, 125, 107, 126, 118, 116, 117, 120, 1, 59, 61, 62, 64, 65, 73, 72; 549/370, 372, 374, 373, 375; 585/269, 20, 21, 24, 25

[56] References Cited

U.S. PATENT DOCUMENTS

| 3,787,512 | 1/1974 | Nelson | 252/299.6 |
| 4,617,142 | 10/1986 | Sugimori | 252/299.63 |
| 4,627,933 | 12/1986 | Eidenschink et al. | 252/299.5 |
| 4,744,918 | 5/1988 | Heppke et al. | 252/299.61 |

FOREIGN PATENT DOCUMENTS

| 23730 | 2/1981 | European Pat. Off. | 252/299.6 |
| 2658610 | 7/1977 | Fed. Rep. of Germany | 252/299.6 |
| 155063 | 5/1982 | German Democratic Rep. | 252/299.63 |
| 155078 | 5/1982 | German Democratic Rep. | 252/299.63 |
| 60-181059 | 9/1985 | Japan | 252/299.6 |
| 60-197637 | 10/1985 | Japan | 252/299.63 |
| 60-204743 | 10/1985 | Japan | 252/299.65 |
| 60-215652 | 10/1985 | Japan | 252/299.63 |
| 60-237048 | 11/1985 | Japan | 252/299.6 |
| 60-246347 | 12/1985 | Japan | 252/299.63 |
| 61-5054 | 1/1986 | Japan | 252/299.63 |
| 62-19561 | 1/1987 | Japan | 252/299.63 |
| 87-5291 | 9/1987 | World Int. Prop. O. | 252/299.63 |

OTHER PUBLICATIONS

Cohen, L. A., et al., J. Amer. Chem. Soc., vol. 95, No. 2, pp. 443–448 (1973).
Ong, B. S., et al., Tetrahedron Lett., No. 37, pp. 3257–3260 (1976).
Demus, D., Nonemissive Electro Optical Displays, pp. 83–119 (1975).
Meiggs, T. O., et al., J. Amer. Chem. Soc., vol. 94, No. 23, pp. 7986–7991 (1972).
Sheehan, M., et al., J. Amer. Chem. Soc., vol. 91, No. 13, pp. 3544–3552 (1969).
Givens, R., et al., J. Org. Chem., vol. 37, No. 26, pp. 4325–4334 (1972).
Rash, F., et al., J. Org. Chem., vol. 32(2), pp. 372–376 (1967).
C. A., vol. 54, 6643b (1960), (p-PrC$_6$H$_4$CH$_2$CH$_2$CH$_2$)$_2$.

Primary Examiner—Teddy S. Gron
Attorney, Agent, or Firm—Millen & White

[57] ABSTRACT

Compounds of the formula

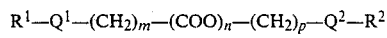

$$R^1-Q^1-(CH_2)_m-(COO)_n-(CH_2)_p-Q^2-R^2$$

wherein
$R^1$ and $R^2$ are each independently alkyl or alkoxy each of 1-12 C atoms, F, Cl, Br, CN or —$Q^3$—$R^3$, or one of $R^1$ and $R^2$ can also be H;
$Q^1$, $Q^2$ and $Q^3$ are each independently 1,4-phenylene, 1,4-cyclohexylene, 1,4-bicyclo(2,2,2)-octylene or 1,3-dioxane-2,5-diyl, each of which is unsubstituted or substituted by 1-4 fluorine, chlorine or bromine atoms;
$R^3$ is alkyl or alkoxy each of 1-8 C atoms, H, F, Cl, Br or CN;
m is 1, 2, 3, 4, 5 or 6; n is 0 or 1; and p is 0, 1, 2, 3, 4 or 5; the sum of (m+p) being 2, 4 or 6 and the sum of (m+n+p) being at least 3;
but with the proviso that $Q^3$ is unsubstituted 1,4-phenylene or 1,4-phenylene substituted by a fluorine, chlorine or bromine atom, only when n=1 or (m+p)=6 or at least one of $R^1$ to $R^3$ is F, Cl or Br or none of $R^1$ to $R^3$ is CN or two of the radicals $R^1$ to $R^3$ are CN, are valuable liquid crystalline components.

14 Claims, No Drawings

RING COMPOUNDS

This is a division of application Ser. No. 511,609, filed July 7, 1983, now U.S. Pat. No. 4,627,933.

SUMMARY OF THE INVENTION

It is an object of this invention to provide new, stable, liquid-crystalline or mesogenic compounds which are suitable for use as components of liquid-crystal dielectrics.

Upon further study of the specification and appended claims, further objects and advantages of this invention will become apparent to those skilled in the art.

These objects have been achieved by providing the compound of Formula I, $$R^1-Q^1-(CH_2)_m-(COO)_n-(CH_2)_p-Q^2-R^2 \qquad I$$

wherein $R^1$ and $R^2$ are each independently alkyl or alkoxy each of 1-12 C atoms, F, Cl, Br, CN or $-Q^3-R^3$ and one of $R^1$ or $R^2$ can also be H;

$Q^1$, $Q^2$ and $Q^3$ are each independently 1,4-phenylene, 1,4-cyclohexylene, 1,4-bicyclo(2,2,2)-octylene or 1,3-dioxane-2,5-diyl, each of which is unsubstituted or substituted by 1-4 fluorine, chlorine and/or bromine atoms;

$R^3$ is alkyl or alkoxy each of 1-8 C atoms, H, F, Cl, Br or CN;

m is 1, 2, 3, 4, 5 or 6; n is 0 or 1; and p is 0, 1, 2, 3, 4 or 5; the sum of (m+p) being 2, 4 or 6 and the sum of (m+n+p) being at least 3;

and wherein $Q^3$ is only a 1,4-phenylene radical which is unsubstituted or substituted by a fluorine, chlorine or bromine atom, when n=1, and/or (m+p)=6, and/or at least one of the radicals $R^1$ to $R^3$ is F, Cl or Br, and/or none of the radicals $R^1$ to $R^3$ is CN, and/or two of the radicals $R^1$ to $R^3$ are CN.

For the sake of simplicity, in the following, "Phe" is 1,4-phenylene, "Cy" is 1,4-cyclohexylene, "Bi" is bicyclo(2,2,2)octylene, and "Dio" is 1,3-dioxane-2,5-diyl. It is possible for these groups, in particular 1,4-phenylene, to be unsubstituted or substituted by 1-4 fluorine, chlorine and/or bromine atoms, when so referred. Furthermore, the group $-(CH_2)_m-(COO)_n-(CH_2)_p-$ is briefly designated "Z" in the following text.

DETAILED DISCUSSION

Similar compounds are known, for example from German Offenlegungsschrift No. 2,617,593. That text discloses, for example, a general formula

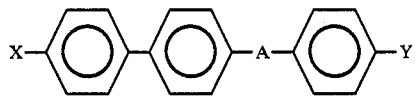

wherein one of the groups X and Y is cyano and the others can, inter alia, also be alkyl or alkoxy and A can, inter alia, also be $-(CH_2)_4-$.

Like similar compounds, for example like those known from German Offenlegungsschrift No. 2,617,593, whose disclosure is incorporated by reference herein, the compounds of Formula I can be used as components of liquid-crystal dielectrics, in particular for displays based on the principle of the twisted cell, the guest-host effect, the effect of the deformation of aligned phases or the effect of dynamic scattering.

It has been found that the compounds of Formula I are excellently suitable for use as components of liquid-crystal dielectrics. In particular, they make it possible to prepare stable liquid-crystal phases which have a broad nematic range and a low viscosity.

In addition, the provision of the compounds of Formula I broadens considerably, in a very general manner, the range of liquid-crystal substances which are suitable, from various points of view relating to applied technology, for the production of nematic mixtures.

The compounds of Formula I possess a broad field of application. Depending on the choice of substituents, these compounds can be used as the base materials from which liquid-crystal dielectrics are principally composed; however, it is also possible to add liquid-crystal base materials belonging to other classes of compounds to the compounds of Formula I, in order, for example to reduce the viscosity or the double refraction of such a dielectric. The compounds of Formula I, particularly those containing cyclohexane or dioxane rings having substituents in the cis-position, and also those wherein $R^1$ and/or $R^2$ are H, Cl, Br or CN, are also suitable for use as intermediate products for the preparation of other substances which can be used as constituents of liquid-crystal dielectrics.

In the pure state, the compounds of Formula I are colorless and form liquid-crystal meso-phases of low viscosity within a temperature range which is advantageously situated for electro-optical use. They are very stable chemically.

The invention thus relates to the compounds of Formula I and to a process for their preparation, comprising treating with a reducing agent, a compound which otherwise corresponds to Formula I, but contains one or more reducible groups and/or C—C bonds instead of H atoms; or, in order to prepare esters of Formula I (n=1), reacting a carboxylic acid of Formula II $$R^1-Q^1-(CH_2)_m-COOH \qquad II$$

wherein $R^1$, $Q^1$ and m are as defined above, or one of its reactive derivatives, with an alcohol or phenol of Formula III $$HO-(CH_2)_p-Q^2R^2 \qquad III$$

wherein $R^2$, $Q^2$ and p are as defined above or with one of its reactive derivatives; or, in order to prepare dioxane derivatives of Formula I wherein at least one of the radicals $Q^1$ to $Q^3$ is a 1,3-dioxane-2,5-diyl group, reacting an appropriate aldehyde with an appropriate 1,3-diol; or, in order to prepare nitriles of Formula I ($R^1$, $R^2$ and/or $R^3$=CN), dehydrating an appropriate carboxamide; or, in order to prepare ethers of Formula I ($R^1$, $R^2$ and/or $R^3$=alkoxy), etherifying an appropriate hydroxy compound; and/or, if appropriate, reacting a chlorine or bromine compound of Formula I ($R^1$, $R^2$ and/or $R^3$=Cl or Br) with a cyanide.

The present invention also relates to the use of the compounds of Formula I as components of liquid-crystal dielectrics. The invention also relates to liquid-crystal dielectrics containing at least one compound of Formula I and also to electro-optical display elements containing dielectrics of this type.

Unless indicated expressly otherwise, in the preceding and following text $R^1$, $R^2$, $R^3$, $Q^1$, $Q^2$, $Q^3$, m, n and p are as defined above.

Accordingly, the compounds of Formula I embrace compounds of the partial formulae Ia to Ip:

$R^1-Q^1-(CH_2)_q-Q^2-R^2$     Ia wherein q is 4 or 6, specifically:

$R^1-Q^1-(CH_2)_4-Q^2-R^2$     Ib and $R^1-Q^1-(CH_2)_6-Q^2-R^2$     Ic;

$R^1-Q^1-(CH_2)_m-COO-(CH_2)_p-Q^2-R^2$     Id specifically:

$R^1-Q^1-CH_2-COO-CH_2-Q^2-R^2$     Ie $R^1-Q^1-CH_2-COO-(CH_2)_3-Q^2-R^2$     If $R^1-Q^1-CH_2-COO-(CH_2)_5-Q^2-R^2$     Ig $R^1-Q^1-(CH_2)_2-COO-Q^2-R^2$     Ih $R^1-Q^1-(CH_2)_2-COO-(CH_2)_2-Q^2-R^2$     Ii $R^1-Q^1-(CH_2)_2-COO-(CH_2)_4-Q^2-R^2$     Ij $R^1-Q^1-(CH_2)_3-COO-CH_2-Q^2-R^2$     Ik $R^1-Q^1-(CH_2)_3-COO-(CH_2)_3-Q^2-R^2$     Il $R^1-Q^1-(CH_2)_4-COO-Q^2-R^2$     Im $R^1-Q^1-(CH_2)_4-COO-(CH_2)_2-Q^2-R^2$     In $R^1-Q^1-(CH_2)_5-COO-CH_2-Q^2-R^2$     Io $R^1-Q^1-(CH_2)_6-COO-Q^2-R^2$     Ip.

Among these, the compounds of the Formulae Ia, Ib, Ic and Ie are particularly preferred.

Compounds of Formula I containing two rings embrace those of the partial Formulae Iq to Iaf, of which those of the Formulae Iq, Ir, Iu, Iv, Iaa and Iaf are particularly preferred:

$R^1-Phe-Z-Phe-R^2$     Iq $R^1-Phe-Z-Cy-R^2$     Ir $R^1-Phe-Z-Bi-R^2$     Is $R^1-Phe-Z-Dio-R^2$     It $R^1-Cy-Z-Phe-R^2$     Iu $R^1-Cy-Z-Cy-R^2$     Iv $R^1-Cy-Z-Bi-R^2$     Iw $R^1-Cy-Z-Dio-R^2$     Ix $R^1-Bi-Z-Phe-R^2$     Iy $R^1-Bi-Z-Cy-R^2$     Iz $R^1-Bi-Z-Bi-R^2$     Iaa $R^1-Bi-Z-Dio-R^2$     Iab $R^1-Dio-Z-Phe-R^2$     Iac $R^1-Dio-Z-Cy-R^2$     Iad $R^1-Dio-Z-Bi-R^2$     Iae $R^1-Dio-Z-Dio-R^2$     Iaf.

Among the compounds of Formula I containing three rings, those of the partial Formulae Iag to Iaj are particularly preferred:

$R^1-Phe-Phe-Z-Phe-R^2$     Iag $R^1-Cy-Phe-Z-Phe-R^2$     Iah $R^1-Phe-Z-Phe-Cy-R^2$     Iai $R^1-Cy-Phe-Z-Cy-R^1$     Iaj.

Among the compounds of the Formula I containing four rings, those of the partial Formula Iak to Iap are particularly preferred:

$R^1-Phe-Phe-Z-Phe-Phe-R^2$     Iak $R^1-Cy-Phe-Z-Phe-Cy-R^2$     Ial $R^1-Dio-Phe-Z-Phe-Dio-R^2$     Iam $R^1-Phe-Cy-Z-Cy-Phe-R^2$     Ian $R^1-Cy-Cy-Z-Cy-Cy-R^2$     Iao $R^1-Dio-Cy-Z-Cy-Dio-R^2$     Iap.

In the compounds of Formula I and also Ia to Iap, the alkyl and/or alkoxy radicals can be linear or branched. Preferably, they are linear, have 2, 3, 4, 5 or 6 C atoms and are, accordingly, preferably, ethyl, propyl, butyl, pentyl, hexyl, ethoxy, propoxy, butoxy, pentoxy or hexyloxy, and also methyl, heptyl, octyl, nonyl, decyl, undecyl, dodecyl, methoxy, heptyloxy, octyloxy, decyloxy, undecyloxy and dodecyloxy.

Compounds of Formula I and also Ia to Iap having branched wing groups $R^1$, $R^2$ or $R^3$ can occasionally be of importance because of superior solubility in the customary liquid-crystal base materials, but are especially of importance as chiral doping substances if they are optically active. As a rule, branched groups of this type contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-heptylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methylheptyloxy.

Specifically, $R_1$ and $R_2$ are preferably alkyl, alkoxy or CN. Preferred compounds among the compounds of Formulae I and also Ia to Iap are those in which at least one of the radicals contained therein has one of the preferred meanings indicated. Minor groups of compounds which are particularly preferred are those of the Formulae Iaq to Ibf:

| | |
|---|---|
| $R^3$—Phe—$(CH_2)_q$—Phe—$R^3$ | Iaq |
| Alkoxy—Phe—$(CH_2)_q$—Phe—Alkoxy | Iar |
| NC—Phe—$(CH_2)_q$—Phe—CN | Ias |
| $R^1$—Phe—$(CH_2)_q$—Phe—CN | Iat |
| $R^3$—Phe—$(CH_2)_q$—Phe—CN | Iau |
| Alkyl—Phe—$(CH_2)_q$—Phe—CN | Iav |
| Alkoxy—Phe—$(CH_2)_q$—Phe—CN | Iaw |
| $R^3$—Cy—Phe—$(CH_2)_q$—Phe—Cy—$R^3$ | Iax |
| Alkyl—Cy—Phe—$(CH_2)_q$—Phe—Cy—Alkyl | Iay |
| $R^1$—Phe—$CH_2$—COO—$CH_2$—$Q^2$—$R^2$ | Iaz |
| $R^1$—Phe—$CH_2$—COO—$CH_2$—Phe—$R^3$ | Iba |
| $R^1$—Phe—$CH_2$—COO—$CH_2$—Phe—CN | Ibb |
| $R^3$—Phe—$CH_2$—COO—$CH_2$—Phe—$R^3$ | Ibc |

(wherein the two $R^3$ groups and the two alkyl or alkoxy groups can be identical or different)

| | |
|---|---|
| $R^3$—Phe—$CH_2$—COO—$CH_2$—Phe—CN | Ibd |
| $R^3$—Cy—Phe—$CH_2$—COO—$CH_2$—Phe—$R^3$ | Ibe |

(wherein the two $R^3$ groups can be identical or different)

| | |
|---|---|
| $R^3$—Cy—Phe—$CH_2$—COO—$CH_2$—Phe—CN | Ibf. |

In the compounds of Formulae I and also Ia to Ibf, preferred stereoisomers are those wherein the substituents on the cyclohexene and/or the dioxanediyl radicals are in each case in the trans-position in relation to one another.

The compounds of Formula I are prepared by methods which are in themselves known, such as are described in the literature (for example in the standard works, such as Houben-Weyl, Methoden der Organischen Chemie ("Methods of Organic Chemistry"), Georg-Thieme-Verlag, Stuttgart), specifically under reaction conditions which are known and suitable for the reactions mentioned. In these methods it is also possible to make use of variants which are in themselves known, but are not mentioned here in greater detail.

If desired, the starting materials can also be formed in situ, in a process in which they are not isolated from the reaction mixture, but are immediately reacted further to give the compounds of Formula I.

The compounds of Formula Ia are preferably prepared by reducing a compound which otherwise corresponds to Formula I, but contains one or more reducible groups and/or C—C bonds instead of H atoms. Suitable reducible groups are preferably carbonyl groups, especially keto groups, and also, for example, free or esterified hydroxyl groups or halogen atoms attached to an aromatic ring. Preferred starting materials for the reduction correspond to the Formula I, but contain the group —CO—$(CH_2)_{m-1}$— instead of the group —$(CH_2)_m$— and/or the group —$(CH_2)_{p-1}$—CO— instead of the group —$(CH_2)_p$— and/or a cyclohexene ring instead of a cyclohexane ring.

Examples of preferred starting materials for the reduction are ketones of the formula $$R^1—Q^1—(CO)_r—(CH_2)_s—(CO)_t—Q^2—R^2 \quad IV$$

wherein r is 0 or 1, s is 2, 3, 4 or 5, t is 0 or 1, the sum of (r+t) is 1 or 2 and the sum of (r+s+t) is 4 or 6. Specifically these are compounds of the following formulae:

$$R^1—Q^1—CO—CH_2—CH_2—CO—Q^2—R^2$$

$$R^1—Q^1—CO—CH_2—CH_2—CH_2—Q^2—R^2$$

$$R^1—Q^1—CH_2—CH_2—CH_2—CO—Q^2—R^2$$

$$R^1—Q^1—CO—(CH_2)_4—CO—Q^2—R^2$$

$$R^1—Q^1—CO—(CH_2)_5—Q^2—R^2$$

$$R^1—Q^1—(CH_2)_5—CO—Q^2—R^2.$$

In these compounds the radical $Q^1$ or $Q^2$ which is attached to the CO group is preferably Phe. These ketones can be obtained, for example, by a Friedel-Crafts reaction between the corresponding aromatic compounds of the formulae $R^1$—Phe—H or H—Phe—$R^2$ and the corresponding acid chlorides of the formulae $$Cl—CO—CH_2CH_2—CO—Cl,$$

$$Cl—CO—(CH_2)_3—Q^2—R^2,$$

$$R^1—Q^1—(CH_2)_3—CO—Cl,$$

$$Cl—CO—(CH_2)_4—CO—Cl,$$

$$Cl—CO—(CH_2)_5—Q^2—R^2 \text{ or}$$

$$R^1—Q^1—(CH_2)_5—CO—Cl.$$

Examples of starting materials containing cyclohexene rings are those of Formula V

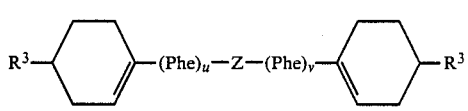

wherein u and v are each 0 or 1.

The starting materials of Formula V can be obtained, for example, by reacting 4-$R^3$-cyclohexanones with organometallic compounds of the formula Li—(-Phe)$_u$—Z—(Phe)$_v$—Li or corresponding Grignard compounds, the resulting carbinols being subsequently dehydrated.

The reduction is preferably effected by catalytic hydrogenation at temperatures of about 0° to about 200° and under pressures of about 1 to about 200 bar in an inert solvent, for example an alcohol, such as methanol, ethanol or isopropanol, an ether such as tetrahydrofuran (THF) or dioxane, an ester, such as ethyl acetate, a carboxylic acid, such as acetic acid, or a hydrocarbon, such as cyclohexane.

Suitable catalysts are preferably noble metals, such as Pt or Pd, which can be employed in the form of oxides (for example $PtO_2$ or PdO), on a support (for example Pd on charcoal, calcium carbonate or strontium carbonate) or in a finely divided form (for example Pt black). The mentioned ketones of Formula IV can also be reduced by the Clemmensen method (using zinc, amalgamated zinc or tin and hydrochloric acid, preferably in an aqueous alcoholic solution or in a heterogeneous phase using water/benzene or water/toluene at temperatures of about 80° to 120°) or the Wolff-Kishner method (using hydrazine, preferably in the presence of an alkali, such as KOH or NaOH, in a high-boiling solvent, such as diethylene glycol or triethylene glycol, at temperatures of about 100° to 200°).

Esters of Formula I ($n=1$) can also be obtained by esterifying corresponding carboxylic acids of Formula II (or their reactive derivatives) with alcohols or phenols of Formula III (or their reactive derivatives).

Suitable reactive derivatives of the mentioned carboxylic acids are, in particular, the acid halides, above all the chlorides and bromides, and also the anhydrides, for example also mixed anhydrides of the formula $R^1-Q^1-(CH_2)_m-CO-O-COCH_3$, azides or esters, especially alkyl esters of 1-4 C atoms in the alkyl group.

Suitable reactive derivatives of the alcohols or phenols mentioned are, in particular, the corresponding metal alcoholates or phenates of the formula $MO-(CH_2)_p-Q^2-R^2$ in which M is one equivalent of a metal, preferably an alkali metal, such as Na or K.

The esterification is advantageously carried out in the presence of an inert solvent. Solvents which are very suitable are, in particular, ethers, such as diethyl ether, di-n-butyl ether, THF, dioxane or anisole, ketones, such as acetone, butanone or cyclohexanone, amides, such as dimethylformamide (DMF) or phosphoric acid hexamethyl triamide, hydrocarbons, such as benzene, toluene or xylene, halogenated hydrocarbons, such as carbon tetrachloride or tetrachloroethylene, and sulfoxides, such as dimethyl sulfoxide or sulfolane. Water-immiscible solvents cn be used advantageously at the same time for removing, by azeotropic distillation, the water formed in the esterification. An excess of an organic base, for example pyridine, quinoline or triethylamine, can also occasionally be used as the solvent for the esterification. The esterification can also be carried out in the absence of a solvent, for example by merely heating the components in the presence of sodium acetate. The reaction temperature is usually −50° to +250°, preferably −20° to +80°. At these temperatures the esterification reactions are complete, as a rule, after 15 minutes to 48 hours.

In individual cases, the reaction conditions for the esterification depend largely on the nature of the starting materials used. Thus a free carboxylic acid is as a rule reacted with a free alcohol or phenol in the presence of a strong acid, for example a mineral acid, such as hydrochloric acid or sulfuric acid. A preferred mode of reaction is to react an acid anhydride or, in particular, an acid chloride with an alcohol, preferably in a basic medium, bases of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification comprises first converting the alcohol or the phenol into the sodium alcoholate or phenate or potassium alcoholate or phenate, for example by treatment with ethanolic sodium hydroxide or potassium hydroxide solution, isolating this alcoholate or phenate and suspending it by stirring in acetone or diethyl ether, together with sodium bicarbonate or potassium carbonate, and adding a solution of the acid chloride or anhydride in diethyl ether, acetone or DMF to this suspension, preferably at temperatures of about −25° to +20°.

Dioxane derivatives of Formula I (wherein one of the groups $Q^1$, $Q^2$ and/or $Q^3$ is 1,3-dioxane-2,5-diyl are preferably prepared by reacting an appropriate aldehyde, for example of the formulae $R^1-CHO$, $R^2-CHO$, $O=CH-Z-Q^2-R^2$ or $R^1-Q^1-Z-CHO$ (or a reactive derivative thereof) with an appropriate 1,3-diol, for example of the formulae $(HOCH_2)_2CH-Z-Q^2R^2$, $R^1-Q^1-Z-CH(CH_2OH)_2$, $R^1CH(CH_2OH)_2$ or $(HOCH_2)_2CH-R^2$ (or one of its reactive derivatives), preferably in the presence of an inert solvent, such as benzene or toluene and/or a catalyst, for example a strong acid, such as sulfuric acid, benzenesulfonic acid or p-toluenesulfonic acid, at temperatures of about 20° to about 150°, preferably 80° to 120°. Suitable reactive derivatives of the starting materials are primarily acetals, for example of the formulae $R^1-CH(OR^4)_2$, $R^2-CH(OR^4)_2$, $(R^4O)_2CH-Z-Q^2-R^2$, $R^1-Q^1-Z-CH(OR^4)_2$, $R^5-CH(OCH_2)_2CH-Z-Q^2-R^2$, $R^1-Q^1-Z-CH(CH_2O)_2CH-R^5$, $R^1-CH(CH_2O)_2-CH-R^5$ or $R^5-CH(OCH_2)_2CH-R^2$, wherein $R^4$ is alkyl of 1–4 C atoms, or two radicals $R^4$ together being alkylene having 2 or 3 C atoms and $R^5$ is H, alkyl of 1–4 C atoms or phenyl.

The mentioned aldehydes and 1,3-diols and also their reactive derivatives are in some cases known. In all cases they can be prepared without difficulty by standard processes of organic chemistry from compounds known from the literature. For example, the aldehydes can be obtained by oxidizing corresponding alcohols or by reducing corresponding carboxylic acids or derivatives thereof, and the diols by reducing corresponding diesters.

In order to prepare nitriles of Formula I ($R^1$, $R^2$ and/or $R^3=CN$), especially those of the Formulae Ias, Iat, Iau, Iav, Iaw, Ibb, Ibd and Ibf, corresponding acid amides, for example those of the Formulae $H_2NCO-Q^1-Z-Q^2-R^2$ or $R^1-Q^1-Z-Q^2-CONH_2$, can be dehydrated. The amides can be obtained, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$ or $COCl_2$, and $P_2O_5$, $P_2S_5$ or $AlCl_3$ (for example in the form of the double compound with NaCl), and aromatic sulfonic acids and sulfonyl halides. This reaction can be carried out in the presence or absence of an inert solvent at temperatures of about 0° to 150°; examples of suitable solvents are bases, such as pyridine or triethylamine, aromatic hydrocarbons, such as benzene, toluene or xylene, or amides, such as DMF.

Alkoxy compounds of Formula I ($R^1$, $R^2$ and/or $R^3$=alkoxy) can be obtained by alkylating corresponding hydroxy compounds, preferably corresponding phenols, it being preferred first to convert the hydroxy compound into a corresponding metal derivative, for example into the corresponding alkali metal alcoholate or alkali metal phenate by treatment with NaOH, KOH, $Na_2CO_3$ or $K_2CO_3$. This alcoholate or phenate can then be reacted with the corresponding alkyl halide or sulfonate or dialkyl sulfate, preferably in an inert solvent, such as acetone, DMF or dimethyl sulfoxide or an excess of aqueous or aqueous-alcoholic NaOH or KOH, at temperatures of about 20° to 100°.

In order to prepare nitriles of Formula I ($R^1$, $R^2$ and/or $R^3$=CN) corresponding chlorine or bromine compounds of the Formula I ($R^1$, $R^2$ and/or $R^3$=Cl or Br) can also be reacted with a cyanide, preferably a metal cyanide, such as NaCN, KCN or $Cu_2(CN)_2$, for example in the presence of pyridine in an inert solvent, such as DMF or N-methylpyrrolidone, at temperatures of 20° to 200°.

All of the starting materials required in the mentioned processes for preparing all of the compounds of this invention are known and/or readily preparable using fully conventional methods beginning with known compounds.

The dielectrics according to this invention comprise 2 to 15, preferably 3 to 12, components, including at least one compound of Formula I. The other constituents are preferably selected from the nematic or nematogenic substances, especially the known substances, belonging to the classes comprising azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines, cyclohexylpyrimidines, phenyldioxanes or cyclohexyldioxanes and, if appropriate, halogenated stilbenes, benzyl phenyl ethers, tolanes and substituted cinnamic acids.

The most important compounds which are suitable as constituents of liquid-crystal dielectrics of this type can be characterized by Formula III

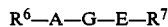

$$R^6-A-G-E-R^7 \qquad III$$

wherein A and E are each a carbocyclic or heterocyclic ring system belonging to the group comprising 1,4-disubstituted benzene and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, dihydronaphthalene, tetrahydronaphthalene, quinazoline and tetrahydroquinazoline; G is

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond; Y is halogen, preferably chlorine, or —CN; and $R^6$ and $R^7$ are alkyl, alkoxy, alkanoyloxy or alkoxycarbonyloxy having up to 18, preferably up to 8, carbon atoms, or one of these radicals is also CN, NC, $NO_2$, $CF_3$, F, Cl or Br.

In most of these compounds, $R^6$ and $R^7$ are different from one another, one of these radicals being an alkyl or alkoxy group in most cases. However, other variants of the envisaged substituents are also customary. Many of such substances or mixtures thereof are commercially available.

The dielectrics according to the invention usually contain about 0.1 to 60, preferably 5 to 40, % of one or more compounds of Formula I.

The dielectrics according to this invention are prepared in a manner which is in itself customary. As a rule, the components are dissolved in one another, preferably at an elevated temperature.

The liquid-crystal dielectrics according to this invention can be modified in such a manner by means of suitable additives that they can be used in all the hitherto disclosed types of liquid-crystal display elements. Additives of this type are known to those skilled in the art and are described in detail in the literature. For example, conducting salts, preferably ethyldimethyldodecylammonium 4-hexyloxybenzoate, tetrabutylammonium tetraphenylboranate or complex salts of crown ethers (compare, for example, I. Haller et al., Mol. Cryst. Liq. Cryst., Volume 24, pages 249–258 (1973)) can be added to improve the conductivity; dichroic dyestuffs can be added in order to prepare colored guest-host systems; or substances can be added to modify the dielectric anisotropy, the viscosity and/or the orientation of the nematic phases. Substances of this type are described, for example, in German Offenlegungsschriften Nos. 2,209,127, 2,240,864, 2,321,632, 2,338,281, 2,450,088, 2,637,430, 2,853,728, and 2,902,177.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

Example 1

A mixture of 48.6 g of 1,2-bis-(p-trans-4-propylcyclohexylbenzoyl)-ethane (obtainable from trans-1-phenyl-4-propylcyclohexane and succinyl chloride in the presence of $AlCl_3$), 30 g of KOH, 50 ml of 85% hydrazine and 500 ml of triethylene glycol is warmed at 120° for 1 hour. The temperature is raised slowly until the dihydrazone formed is decomposed. The mixture is boiled for a further 4 hours and cooled and worked up in a customary manner to give 1,4-bis-(p-trans-4-propylcyclohexylphenyl)-butane, m.p. 136°, c.p. 158°.

The following compounds are obtained analogously by Wolff-Kishner reduction of the appropriate diketones:

1,4-Bis-p-methoxyphenylbutane
1,6-Bis-p-methoxyphenylhexane, m.p. 71°, c.p. −25°
1,4-Bis-p-ethoxyphenylbutane
1,6-Bis-p-ethoxyphenylhexane
1,4-Bis-p-propoxyphenylbutane
1,6-Bis-p-propoxyphenylhexane
1,4-Bis-p-dodecyloxyphenylbutane
1,4-Bis-p-tolylbutane
1,6-Bis-p-tolylhexane
1,4-Bis-p-ethylphenylbutane
1,6-Bis-p-ethylphenylhexane
1,4-Bis-p-propylphenylbutane
1,6-Bis-p-propylphenylhexane
1,4-Bis-p-butylphenylbutane
1,6-Bis-p-butylphenylhexane
1,4-Bis-p-pentylphenylbutane
1,6-Bis-p-pentylphenylhexane
1,4-Bis-p-dodecylphenylbutane
1,4-Bis-p-fluorophenylbutane 1,6-Bis-p-fluorophenylhexane
1,4-Bis-p-chlorophenylbutane
1,6-Bis-p-chlorophenylhexane
1,4-Bis-p-bromophenylbutane
1,6-Bis-p-bromophenylhexane
1,4-Bis-p-cyanophenylbutane
1,6-Bis-p-cyanophenylhexane
1,4-Bis-(p-trans-4-butylcyclohexylphenyl)-butane
1,6-Bis-(p-trans-4-butylcyclohexylphenyl)-hexane
1,4-Bis-(p-trans-4-pentylcyclohexylphenyl)-butane
1,6-Bis-(p-trans-4-pentylcyclohexylphenyl)-hexane

Example 2

1,4-Bis-(p-trans-4-propylcyclohexylphenyl)-butane, m.p. 136°, c.p. 158°, is obtained analogously to Example 1 by a Wolff-Kishner reaction from 47.1 g of 1-(p-trans-4-propylcyclohexylbenzoyl)-3-(p-trans-4-propylcyclohexylphenyl)-propane [obtainable from 4-(p-trans-4-propylcyclohexylphenyl)-butyryl chloride and trans-1-phenyl-4-propylcyclohexane].

Example 3

A solution of 51.4 g of 1,4-bis-(p-trans-4-propylcyclohexylbenzoyl)-butane (obtainable from trans-1-phenyl-4-propylcyclohexane and adipoyl chloride in the presence of AlCl$_3$) in 500 ml of THF is hydrogenated over 5g of 10% Pd-on-C at 40° and 1 bar until absorption of H$_2$ ceases. The mixture is filtered and evaporated to give 1,6-bis-(p-trans-4-propylcyclohexylphenyl)-hexane, m.p. 107°, c.p. 129°.

The following are obtained analogously by hydrogenating the corresponding diketones:
1,4-Bis-(4'-methoxy-4-biphenylyl)-butane
1,4-Bis-(4'-ethoxy-4-biphenylyl)-butane.

Example 4

A solution of 45.4 g of 1,4-bis-(p-propylcyclohexen-1-ylphenyl)-butane [obtainable by reacting 1,4-bis-(p-bromomagnesiophenyl)-butane with 4-propylcyclohexanone, subsequently hydrolyzing the product to give 1,4-bis-(p-(4-propyl-1-hydroxycyclohexyl)-phenyl)-butane and dehydrating the latter with p-toluenesulfonic acid in boiling toluene] in 600 ml of THF is hydrogenated over 5 g of PdO at 40° and 1 bar until hydrogen absorption ceases. The mixture is filtered and evaporated and the resulting cis-trans mixture is dissolved in 200 ml of DMF, 14 g of K tert-butylate is added and the mixture is heated at 100° for 24 hours under N$_2$. After cooling, the mixture is poured into water and the resulting 1,4-(bis-(p-trans-4-propylcyclohexylphenyl)-butane is filtered off; m.p. 136°, c.p. 158°.

The following are obtained analogously by hydrogenating the corresponding cyclohexene derivatives:
1,4-Bis-(trans-4-propylcyclohexyl)-butane
1,6-Bis-(trans-4-propylcyclohexyl)-hexane
1,4-Bis-(trans-4-butylcyclohexyl)-butane
1,6-Bis-(trans-4-butylcyclohexyl)-hexane
1,4-Bis-(trans-4-pentylcyclohexyl)-butane
1,6-Bis-(trans-4-pentylcyclohexyl)-hexane.

Example 5

28.8 g of p-(trans-4-pentylcyclohexyl)-phenylacetic acid is boiled for 1 hour with 24 g of SOCl$_2$; the mixture is evaporated; the crude acid chloride obtained is dissolved in 150 ml of toluene, 8 ml of pyridine and 13.3 g of p-cyanobenzyl alcohol are added; and the mixture is boiled for 2 hours. Cooling and working up in a customary manner give p-cyanobenzyl p-(trans-4-pentylcyclohexyl)-phenylacetate, m.p. 85°, c.p. 30°.

The following are obtained analogously by esterifying the corresponding acids:
p-cyanobenzyl p-methoxyphenylacetate
p-cyanobenzyl p-ethoxyphenylacetate
p-cyanobenzyl p-propoxyphenylacetate
p-cyanobenzyl p-(trans-4-propylcyclohexyl)-phenylacetate
p-cyanobenzyl p-(trans-4-butylcyclohexyl)-phenylacetate
p-fluorobenzyl p-(trans-4-pentylcyclohexyl)-phenylacetate
p-chlorobenzyl p-(trans-4-pentylcyclohexyl)-phenylacetate
p-bromobenzyl p-(trans-4-pentylcyclohexyl)-phenylacetate
trans-4-propylcyclohexylmethyl p-methoxyphenylacetate
3-p-cyanophenylpropyl p-cyanophenylacetate
5-p-cyanophenylpentyl p-fluorophenylacetate
p-cyanophenyl 3-phenylpropionate
p-cyanophenyl 3-(p-trans-4-propylcyclohexyl-phenyl)-propionate, m.p. 91°, c.p. 108°
p-ethoxyphenyl 3-(p-trans-4-propylcyclohexyl-phenyl)-propionate
p-butoxyphenyl 3-(p-trans-4-propylcyclohexyl-phenyl)-propionate, m.p. 75°, c.p. 101°
p-propylphenyl 3-(p-trans-4-propylcyclohexyl-phenyl)-propionate
p-pentylphenyl 3-(p-trans-4-propylcyclohexyl-phenyl)-propionate, m.p. 65°, c.p. 74°
p-heptylphenyl 3-(p-trans-4-propylcyclohexyl-phenyl)-propionate
p-fluorophenyl 3-(p-trans-4-propylcyclohexyl-phenyl)-propionate, m.p. 97°, c.p. 55° (monotropic)
p-cyanophenyl 3-(p-trans-4-pentylcyclohexyl-phenyl)-propionate
p-ethoxyphenyl 3-(p-trans-4-pentylcyclohexyl-phenyl)-propionate
p-butoxyphenyl 3-(p-trans-4-pentylcyclohexyl-phenyl)-propionate
p-propylphenyl 3-(p-trans-4-pentylcyclohexyl-phenyl)-propionate
p-pentylphenyl 3-(p-trans-4-pentylcyclohexyl-phenyl)-propionate
p-heptylphenyl 3-(p-trans-4-pentylcyclohexyl-phenyl)-propionate
p-fluorophenyl 3-(p-trans-4-pentylcyclohexyl-phenyl)-propionate
2-p-cyanophenylethyl 3-p-methoxyphenylpropionate
4-p-cyanophenylbutyl 3-p-chlorophenylpropionate
p-cyanobenzyl 4-p-ethoxyphenylbutyrate
3-p-cyanophenylpropyl 4-p-ethoxyphenylbutyrate
p-cyanophenyl 5-p-ethoxyphenylpentanoate
2-p-cyanophenylethyl 5-p-ethoxyphenylpentanoate
p-cyanobenzyl 6-p-ethoxyphenylhexanoate
p-cyanophenyl 7-p-ethoxyphenylheptanoate.

Example 6

A mixture of 1 g of hexanal, 2.5 g of 2-(4-p-propylphenylbutyl)-propane-1,3-diol (obtainable by reacting diethyl malonate with 4-p-propylphenylbutyl bromide to give diethyl 2-(4-p-propylphenylbutyl)-malonate and reducing the latter with LiAlH$_4$), 0.01 g of p-toluenesulfonic acid and 15 ml of toluene is boiled for 3 hours under a water separator and is cooled, washed with water and evaporated. This gives 2-pentyl-5-(4-p-propylphenylbutyl)-1,3-dioxane.

The following are obtained analogously by reacting the correspondong aldehydes with the corresponding diols:
2-propyl-5-(4-p-propylphenylbutyl)-1,3-dioxane
2-propyl-5-(4-p-butylphenylbutyl)-1,3-dioxane
2-propyl-5-(4-p-pentylphenylbutyl)-1,3-dioxane
2-butyl-5-(4-p-propylphenylbutyl)-1,3-dioxane
2-butyl-5-(4-p-butylphenylbutyl)-1,3-dioxane
2-butyl-5-(4-p-pentylphenylbutyl)-1,3-dioxane
2-pentyl-5-(4-p-butylphenylbutyl)-1,3-dioxane
2-pentyl-5-(4-p-pentylphenylbutyl)-1,3-dioxane

Example 7

65 g of POCl$_3$ is added dropwise at 50° and while stirring to a solution, in 500 ml of DMF, of 31.3 g of p-carbamoylbenzyl p-ethoxyphenylacetate (obtainable by esterification). After stirring for a further hour, the mixture is poured onto ice and worked up in a customary manner to give p-cyanobenzyl p-ethoxyphenylacetate, m.p. 59°, c.p. −40°.

The following are obtained analogously by dehydrating the corresponding amides:
1-p-methoxyphenyl-4-p-cyanophenylbutane
1-p-methoxyphenyl-6-p-cyanophenylhexane
1-p-ethoxyphenyl-4-p-cyanophenylbutane
1-p-ethoxyphenyl-6-p-cyanophenylhexane
1-p-propoxyphenyl-4-p-cyanophenylbutane
1-p-propoxyphenyl-6-p-cyanophenylhexane
1-p-tolyl-4-p-cyanophenylbutane
1-p-tolyl-6-p-cyanophenylhexane
1-p-ethylphenyl-4-p-cyanophenylbutane
1-p-ethylphenyl-6-p-cyanophenylhexane
1-p-propylphenyl-4-p-cyanophenylbutane
1-p-propylphenyl-6-p-cyanophenylhexane
1-p-butylphenyl-4-p-cyanophenylbutane
1-p-butylphenyl-6-p-cyanophenylhexane
1-p-pentylphenyl-4-p-cyanophenylbutane
1-p-pentylphenyl-6-p-cyanophenylhexane.

Example 8

A mixture of 26.8 g of 1-p-propylphenyl-4-p-hydroxyphenylbutane, 6.9 g of K$_2$CO$_3$, 25 g of hexyl iodide and 250 ml of DMF is heated at 80° for 16 hours, while stirring, and is then cooled and worked up in a customary manner. This gives 1-p-propylphenyl-4-p-hexoxyphenylbutane.

The following are obtained analogously by etherification:
1-p-propylphenyl-4-p-methoxyphenylbutane
1-p-propylphenyl-6-p-methoxyphenylhexane
1-p-butylphenyl-4-p-methoxyphenylbutane
1-p-butylphenyl-6-p-methoxyphenylhexane
1-p-pentylphenyl-4-p-methoxyphenylbutane
1-p-pentylphenyl-6-p-methoxyphenylhexane.

Example 9

A mixture of 34.9 g of p-bromobenzyl p-ethoxyphenylacetate (obtainable by esterification), 10 g of Cu$_2$(CN)$_2$, 120 ml of pyridine and 60 ml of N-methylpyrrolidone is heated at 150° for 2 hours. The mixture is cooled; a solution of 120 g of FeCl$_3$.6H$_2$O in 600 ml of 20% hydrochloric acid is added; and the mixture is warmed at 70° for 1.5 hours while stirring and worked up in a customary manner to give p-cyanobenzyl p-ethoxyphenylacetate, m.p. 59°, c.p. −40°.

The following are obtained analogously from 1,4-bis-p-bromophenylbutane and from 1,6-bis-p-bromophenylhexane, respectively:
1,4-bis-p-cyanophenylbutane
1,6-bis-p-cyanophenylhexane.

The following are examples of dielectrics according to the invention containing at least one compound of Formula I:

Example A

A mixture of:
15% of p-(trans-4-propylcyclohexyl)-benzonitrile
11% of p-(trans-4-butylcyclohexyl)-benzonitrile
21% of p-(trans-4-pentylcyclohexyl)-benzonitrile
15.5% of 1,6-bis-(p-methoxyphenyl)-hexane
21% of 4-ethyl-4'-(trans-4-pentylcyclohexyl)-biphenyl
12% of 4-(trans-4-pentylcyclohexyl)-4'-(trans-4-propylcyclohexyl)-biphenyl and
4.5% of 4-cyano-4'-(trans-4-pentylcyclohexyl)-biphenyl
has m.p. 0°, c.p. 94°.

Example B

A mixture of:
15% of p-(trans-4-propylcyclohexyl)-benzonitrile
27% of trans-1-p-ethylphenyl-4-propylcyclohexane
10% of trans-1-p-ethoxyphenyl-4-propylcyclohexane
7% of 4-cyano-4'-(trans-4-pentylcyclohexyl)-biphenyl
8% of 1,4-bis-(p-trans-4-propylcyclohexylphenyl)-butane
10% of 4-(trans-4-pentylcyclohexyl)-4'-(trans-4-propylcyclohexyl)-biphenyl
8% of p-propylphenyl p-(trans-4-propylcyclohexyl)-benzoate
6% of p-propylphenyl p-(trans-4-pentylcyclohexyl)-benzoate
9% of 4-ethyl-4'-(trans-4-propylcyclohexyl)-biphenyl
has m.p. −5°, c.p. 85°.

The preceding examples can be repeated with similar success by substituting the generically or specifically described reactants and/or operating conditions of this invention for those used in the preceding examples. From the foregoing description, one skilled in the art can easily ascertain the essential charcteristics of this invention, and without departing from the spirit and scope thereof, can make various changes and modifications of the invention to adapt it to various usages and conditions.

What is claimed is:

1. A ring compound of the formula

wherein
R$^1$ and R$^2$ are each independently alkyl or alkoxy each of 1-12 C atoms, F, Cl, Br, CN, or —Q$^3$—R$^3$, or one of R$^1$ and R$^2$ can also be H, and at least one or R$^1$ and R$^2$ is —Q$^3$—R$^3$;
Q$^1$, Q$^2$ and Q$^3$ are each independently 1,4-phenylene (Phe), 1,4-cyclohexylene (Cy), 1,4-bicyclo(2,2,2)-octylene (Bi) or 1,3-dioxane-2,5-diyl (Dio), each of which is unsubstituted or substituted by 1-4 fluorine, chlorine or bromine atoms;
R$^3$ is alkyl or alkoxy each of 1-8 C atoms, H, F, Cl, Br or CN;
m is 2; n is 1; and p is 0, 2, or 4;
but with the proviso that R$^1$—Q$^1$ is not alkyl-Cy when p=0.

2. A compound of claim 1 of the formula

R³—Phe—Phe—Z—Phe—R²

R³—Cy—Phe—Z—Phe—R²

R¹—Phe—Z—Phe—Cy—R³

R³—Cy—Phe—Z—Cy—R² wherein Phe is 1,4-phenylene, Cy is 1,4-cyclohexylene and Z is —(CH$_2$)$_m$—(COO)$_n$—(CH$_2$)$_p$—.

3. A compound of claim 1 of the formula

R³—Phe—Phe—Z—Phe—Phe—R³

R³—Cy—Phe—Z—Phe—Cy—R³

R³—Dio—Phe—Z—Phe—Dio—R³

R³—Phe—Cy—Z—Cy—Phe—R³

R³—Cy—Cy—Z—Cy—Cy—R³

R³—Dio—Cy—Z—Cy—Dio—R³ wherein "Phe" is 1,4-phenylene, "Cy" is 1,4-cyclohexylene, "Dio" is 1,3-dioxane-2,5-diyl and Z is —(CH$_2$)$_m$—(COO)$_n$(CH$_2$)$_p$—.

4. A compound of claim 1 wherein all alkyl and alkoxy groups are straight chained.

5. A compound of claim 1 wherein R¹ or R² is independently alkyl, alkoxy or CN.

6. A liquid-crystal dielectric useful for electro-optical display elements and comprising at least two liquid-crystal components, wherein at least one of the components is a compound of claim 1.

7. A dielectric of claim 6 comprising 2–15 liquid crystal components.

8. In an electro-optical display element comprising a liquid crystal dielectric, the improvement wherein the dielectric is that of claim 6.

9. A compound of claim 1 of the formula

R¹—Q¹—(CH$_2$)$_2$—COO—Q²—R².

10. A liquid-crystal dielectric useful for electro-optical display elements and comprising at least two liquid-crystal components, wherein at least one of the components is a compound of claim 9.

11. In an electro-optical display element comprising a liquid crystal dielectric, the improvement wherein the dielectric is that of claim 10.

12. A dielectric of claim 10, wherein all Q groups are 1,4-cyclohexylene or 1,4-phenylene, unsubstituted or substituted.

13. A dielectric of claim 12, wherein one of Q¹ and Q² is 1,4-phenylene and, respectively, one of R² and R¹ is —Q³—R³.

14. A dielectric of claim 13, wherein Q² and Q³, or Q¹ and Q³, respectively, are both 1,4-cyclohexylene.

* * * * *